United States Patent
Knudsen

(10) Patent No.: US 8,758,840 B2
(45) Date of Patent: Jun. 24, 2014

(54) METHOD OF TREATING AREAS OF OSTEOARTHRITIS IN ANIMALS AND HUMAN BEINGS WITH MILKWEED SEED OIL

(75) Inventor: Herbert D. Knudsen, Ogallala, NE (US)

(73) Assignee: Natural Fibers Corporation, Ogallala, NE (US)

( * ) Notice: Subject to any disclaimer, the term of this patent is extended or adjusted under 35 U.S.C. 154(b) by 317 days.

(21) Appl. No.: 13/066,125

(22) Filed: Apr. 7, 2011

(65) Prior Publication Data

US 2012/0258186 A1 Oct. 11, 2012

(51) Int. Cl.
*A61K 36/00* (2006.01)
*A61K 36/27* (2006.01)

(52) U.S. Cl.
USPC .......................................... 424/776; 424/725

(58) Field of Classification Search
None
See application file for complete search history.

(56) References Cited

U.S. PATENT DOCUMENTS

| 2001/0024664 A1* | 9/2001 | Obukowicz et al. .......... 424/725 |
| 2006/0024356 A1* | 2/2006 | Waldron et al. ............... 424/442 |
| 2011/0038943 A1 | 2/2011 | Knudsen |

FOREIGN PATENT DOCUMENTS

| WO | WO 2010/002880 A1 * | 1/2010 |
| WO | WO2011/019387 | 2/2011 |

OTHER PUBLICATIONS

Filajdic, Composition of fatty acids of common milkweed-oil seeds determined by macro-, semimicro-, and microanalysis, Kem. I Ind (Zagreb ( (1961), 10: 5-10.*
Silberberg et al, Modifying effect of linoleic acid on articular aging and osteoarthrosis in lard-fed mice, Gerontologia 11: 179-187.*
Matzurevich, The oil from the seeds of *Asclepias cornuti*, Zhurnal Prikladnoi Khimli (1936), 9, 509-517.*
Gabay, et al, "Osteoarthritis and Cartilage-Stigmasterol: a phytosterol with potential anti-osteoarthritic properties." (2010) 106-116 OARSI.

* cited by examiner

*Primary Examiner* — Qiuwen Mi
(74) *Attorney, Agent, or Firm* — Dennis L. Thomte; Thomte Patent Law Office LLC

(57) ABSTRACT

A method of administering milkweed seen oil to areas of osteoarthritis in animals and human beings is disclosed to alleviate symptoms associated with osteoarthritis.

17 Claims, No Drawings

METHOD OF TREATING AREAS OF OSTEOARTHRITIS IN ANIMALS AND HUMAN BEINGS WITH MILKWEED SEED OIL

BACKGROUND OF THE INVENTION

1. Field of the Invention

This invention relates to a method of improving the health of animals and human beings suffering from osteoarthritis. More particularly, this invention relates to a method wherein milkweed seed oil is applied to those areas of the animal or human being affected with osteoarthritis.

2. Description of the Related Art

In the United States, 27 million people suffer from osteoarthritis, the leading cause of chronic disability in this country. Traditional treatment of osteoarthritis involves a combination of exercise, lifestyle modification and analgesics. If the pain becomes debilitating, joint replacement surgery of the affected join is used to improve the quality of life of the animal or human being. Human health and animal health is monitored by the amount of pain experienced and the amount of pain medication that is needed to control the pain experienced. Effective and positive treatments of osteoarthritis are sought.

In laboratory tests, Gabay et. al. in *Osteoarthritis and Cartilage*, January 2010; Vol. 18(1):106-16, show that the phytosterols, stigmasterol, " . . . inhibits several pro-inflammatory and matrix degradation mediators typically involved in osteoarthritis-induced cartilage degradation."

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

In this invention, milkweed seed oil is administered to animals or humans to alleviate osteoarthritis symptoms in the animal or human being, especially pain. The improvement in health is evidenced by the reduction in pain medications used to control the pain.

The milkweed seed oil of this invention is a product consisting of fatty acids and lesser quantities of other ingredients. The milkweed seed oil is administered topically, orally or, internally injected into the animal or human being in an amount and for a period of time that positively affects the animal or human pain relief from osteoarthritis.

These and other objects will be apparent to those skilled in the art.

DESCRIPTION OF THE PREFERRED EMBODIMENT

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

In this invention, milkweed seed oil is administered to animals or humans to alleviate osteoarthritis symptoms in the animal or human being, especially pain. The improvement in health is evidenced by the reduction in pain medications used to control the pain.

The milkweed seed oil of this invention is a product consisting of fatty acids and lesser quantities of other ingredients. The milkweed seed oil is administered topically, orally or internally injected into the animal or human being in an amount and for a period of time that positively affects the animal or human pain relief from osteoarthritis.

The milkweed seed oil of the invention is produced from the seeds found in the pods of milkweed plants, which are known under the Latin binomial name *Asclepias*. Any of the numerous *Asclepias* plants can be used as a source of seeds for producing milkweed seed oil. The most prominent sources of milkweed seeds in the work on this invention to date are seeds from *Asclepias Syriaca* and *Asclepias Specosia*.

The milkweed seed oil of this invention is produced by cold pressing substantially clean milkweed seeds in a seed press or by extracting the oil from the seed with a non-polar solvent to recover the milkweed seed oil. Suitable non-polar solvents include but are not limited to hexane, carbon dioxide and petroleum ether. These solvents produce a liquid lipid product consisting of fatty acids.

Raw milkweed seed oil produced in pressing equipment or in extraction with a solvent needs to be filtered to remove the fine particles of the milkweed seed. This can be accomplished with traditional seed oil separating equipment, efficient filtration systems or other means of separation.

A typical fatty acid profile of milkweed seed oil produced in a seed press is shown below in Table 1. As can be deduced from the data, the milkweed seed oil has a large majority of fatty acids commonly found in food grade vegetable oils. The oil also contains two less common fatty acids C16:1 palmitoleic acid and C18:1 cis-vaccenic acid. The milkweed seed oil with the fatty acid profile in Table 1 was used in the experiments described below.

TABLE 1

Fatty Acid Profile of Milkweed Seed Oil

| | | Percent |
|---|---|---|
| C16:0 | Palmitic Acid | 6.6 |
| C16:1 | Palmitoleic Acid | 11.8 |
| C17:0 | Heptadecanoic Acid | 2.4 |
| C17:1 | 10-Heptadecanoic Acid | 0.2 |
| C18:0 | Stearic Acid | 0.2 |
| C18:1 n9 | Oleic Acid | 23.9 |
| C18:1 n7 | Vaccenic Acid | 12.4 |
| C18:2 | Linoleic Acid | 40.4 |
| C18:3 | Linolenic | 1.3 |
| C20:0 | Arachidic Acid | 0.5 |
| C20:1 | Eicosenoic Acid | 0.2 |
| C22:2 | Docosadienoic Acid | 0.4 |
| C23:0 | Tricosanoic Acid | 0.4 |
| C24:0 | Lignoceric Acid | 0.4 |
| C24:1 | Nervonic Acid | 0.2 |

Milkweed seed oil also contains other ingredients in lesser amounts. Other ingredients identified in the oil used in the experiment below include:

Phospholipids, 2.15 g/100 g
Digitoxin like components, 890 mg/100 g
Stigmasterol, 272.8 mg/100 g
Alpha Tocopherol, 37.8 mg/100 g
B-sitosterol, 23.7 mg/100 g
Campesterol, 13.6 mg/100 g Vitamins, phytosterols, carotenes and other trace ingredients found in milkweed seed oil have a positive impact on animal or human health even at very low concentrations.

Milkweed seed used to produce milkweed seed oil differs based on the genetic line of *Asclepias* used in production, the weather during the milkweed pod growth and the geographical region where the milkweed was grown. These variations are within the limits of the current invention.

Some of the factors affecting the application of milkweed seed oil to animals and humans will now be discussed. Milkweed seed oil can be administered to animals or humans topically, orally or internally. The amount administered daily measured as 100% milkweed seed oil should be less than 5 grams per kilogram of body weight with less than one gram per kilogram of body weight being preferred. Lower amounts of milkweed seed oil, such as 0.1 gram per kilogram of body weight and even 0.01 gram per kilogram of body weight have been proven effective.

For topical applications, milkweed seed oil can be administered by hand or any other application technique to any area of the skin adjacent to the painful joint. The milkweed seed oil penetrates through the skin quickly.

The milkweed seed oil liquid formulation administered to an animal or human being may be milkweed seed oil alone or milkweed seed oil in combination with other ingredients that do not block the beneficial effect of milkweed seed oil. Formulated compositions of liquid milkweed seed oil and other components are preferred embodiments of this invention. The concentration of milkweed seed oil in the preferred formulations contains 50% or more of milkweed seed oil, with formulations containing 70% or more of milkweed seed oil being preferred and formulations containing 15% or more of milkweed seed oil being especially useful.

Possible compatible ingredients in milkweed seed oil liquid formulations include food grade vegetable oils, nut oils, fragrances and other seed oils. Jojoba oil is also an effective combination with milkweed seed oil. Possible vegetable oils include but are not limited to olive oil, canola oil, safflower oil, corn oil, soybean oil, sunflower seed oil and flax oil. Possible nut oils include but are not limited to walnut oil, almond oil and macadamia nut oil. A wide range of fragrances are available commercially that could be used to alter the flavor of the milkweed seed oil product formulation.

The dosage of the milkweed seed oil administered to an animal or human being depends on the concentration of the milkweed seed oil in the formulation. In topical applications using a 77% milkweed seed oil blend, excellent results have been obtained on a 93 kilogram animal using a dose of 0.3 gram per application 2 times per day in separated periods of time. Administering this amount to the animal or human being is a daily amount of 0.006 grams per kilogram of body weight. This dosage is within the most preferred daily rate of administration—less than 0.01 grams per kilogram of body weight. The same amount of milkweed seed oil could be administered using one gram doses of a blend containing 25% milkweed seed oil and 75% vegetable or jojoba oil.

Evidence indicates that total daily use of less than 1 gram of milkweed seed oil, calculated as 100% oil, is more than sufficient to produce the desired improvement in osteoarthritis pain. The dosage of milkweed seed oil taken orally or internally rather than topically may vary from these general guidelines for topical applications. Experience has shown that the animal administered milkweed seed oil topically demonstrate the impact of the formulation on the body of the animal. Changes in the dosage may be necessary in response to these observations.

The optimum milkweed seed oil applications have not been fully evaluated. The best data points to date are the experimental tests below. Higher dosages or longer usage of milkweed seed oil could further improve the joint health. It may be necessary to continue milkweed seed oil treatment to maintain the improved pain relief results, but there is evidence that milkweed seed oil has a positive impact on joint pain for a few days after daily consumption terminates. The need to have an effective amount of milkweed seed oil may require the user to alter the dosage over time to provide the desired benefits as measured by the difference in the level of pain.

EXPERIMENT NO. 1

In this experiment, clean milkweed seeds from *Asclepias Syriaca* and *Asclepias Specosia* plants were pressed in a screw press to produce raw milkweed seed oil. The raw oil was strained in two layers of high thread count cotton fabric at atmospheric pressure to produce clean milkweed seed oil. The clean milkweed seed oil was placed in a marked container, sealed and placed in a constant temperature room maintained at about 70 degrees Fahrenheit. Samples of milkweed seed oil for the experiments described below were taken from the stored oil and maintained in marked sealed bottles. The fatty acid profile of milkweed seed oil produced in this experiment is shown above in Table 1.

EXPERIMENT NO. 2

A test to determine the impact of milkweed seed oil treatment was conducted on a 69 year old male human being weighing 195 pounds. For more than one year before the test began, the male had been taking 20 mg of Lipitor®, 6.25 mg of Hyzaar®, one aspirin tablet and vitamin supplements daily. During that two year period previous to the test, the male ate a regular healthy diet without restriction and exercised for 15 to 25 minutes per day. The male had increasing pain in his left hip joint. To cope with this pain, the male took 2 to 8 ibuprofen tablets of 200 mg each. The male's personal doctor took an x-ray of the male's hips and found that osteoarthritis had degraded the cartilage in the hip joint to the point where bone-on-bone friction was experienced. After confirmation of this bone-on-bone friction with an orthopedic surgeon, the male applied 3 drops of a blend of 77% milkweed seed oil and 23% jojoba oil on his back adjacent to the defective left hip joint twice a day, once in the morning and once in the evening before bed. From the first treatment, the male experienced little or no pain. As a result no ibuprofen pain relievers were taken. This milkweed seed oil blend administration was continued for 42 days without any debilitating hip joint pain and with no need to take any additional form of pain relief like ibuprofen.

The dramatic improvement in the pain relief was unexpected.

There are many possible treatments of animals or humans with milkweed seed oil to control osteoarthritis pain. The description of this basic invention can lead others skilled in the art to identify and apply these treatments using milkweed seed oil.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. A method for reducing the symptoms of osteoarthritis in the joint of a human being by administering an effective amount of milkweed seed o to the area around the affected joint of the human being.

2. The method of claim 1 wherein the amount of milkweed seed oil administered to a human being per day is less than 5 grams per kilogram of body weight.

3. The method of claim 1 wherein the amount of milkweed seed oil administered to a human being per day is less than 0.1 grams per kilogram of body weight.

4. The method of claim 1 wherein the amount of milkweed seed oil administered to a human being per day is less than 0.01 grams per kilogram of body weight.

5. The method of claim 1 wherein the symptom of osteoarthritis is pain.

6. A method for reducing the symptoms of osteoarthritis in the joint of an animal by administering an effective amount of milkweed seed oil containing linoleic acid to the area and phytosterols selected from the group consisting of digitoxin-like components, stigmasterol, beta-sitosterol, alpha tocopherol, campesterol and mixtures thereof around the affected joint of the animal.

7. The method of claim 6 wherein the amount of milkweed seed oil administered to the animal per day is less than 5 grams per kilogram of body weight.

8. The method of claim 6 wherein the amount of milkweed seed oil administered to the animal per day is less than 0.1 grams per kilogram of body weight.

9. The method of claim 6 wherein the amount of milkweed seed oil administered to the animal per day is less than 0.01 grams per kilogram of body weight.

10. The method of claim 6 wherein the symptom of osteoarthritis is pain.

11. The method of claim 6 wherein the milkweed seed oil contains approximately 40.4 percent linoleic acid.

12. A method for reducing the symptoms of osteoarthritis in the joint of a human being by administering an effective amount of milkweed seed oil to the area around the affected joint of the human being, with the milkweed seed oil containing linoleic acid and phytostero selected from the group consisting of digitoxin-like components, stigmasterol, beta-sitosterol, alpha tocopherol, campesterol and mixtures thereof.

13. The method of claim 12 wherein the amount of milkweed seed oil administered to a human being per day is less than 5 grams per kilogram of body weight.

14. The method of claim 12 Wherein the amount of milkweed seed oil administered to a human being per day is lees than 0.1 grams per kilogram of body weight.

15. The method of claim 12 wherein the amount of milkweed seed oil administered to a human being per day is less than 0.01 grams per kilogram of body weight.

16. The method of claim 12 wherein the symptom of symptom of osteoarthritis is pain.

17. The method of claim 12 wherein the milkweed seed oil contains approximately 40.4 percent linoleic acid.

* * * * *